United States Patent [19]
Graebe

[11] Patent Number: 4,730,610
[45] Date of Patent: Mar. 15, 1988

[54] FOOT AND ELBOW CUSHION DEVICE

[76] Inventor: Robert H. Graebe, 4 Signal Hill Boulevard, Belleville, Ill. 62223

[21] Appl. No.: 820,211

[22] Filed: Jan. 21, 1986

Related U.S. Application Data

[63] Continuation-in-part of Ser. No. 730,467, May 6, 1985, abandoned.

[51] Int. Cl.⁴ .............................................. A61B 19/00
[52] U.S. Cl. ............................ 128/149; 128/DIG. 20
[58] Field of Search .............. 128/77, 85, 87 R, 89 R, 128/90, DIG. 20, 149; 5/455

[56] References Cited

U.S. PATENT DOCUMENTS

| | | | |
|---|---|---|---|
| 2,028,060 | 1/1936 | Gilbert | 128/DIG. 20 X |
| 2,531,074 | 11/1950 | Miller | 128/DIG. 20 X |
| 3,850,167 | 11/1974 | Seeley | 128/89 R X |
| 4,005,236 | 1/1977 | Graebe | 5/455 |
| 4,378,009 | 3/1983 | Rowley et al. | 128/DIG. 20 X |
| 4,471,770 | 9/1984 | Pompa | 128/149 X |
| 4,497,316 | 2/1985 | Lilla | 128/77 |

Primary Examiner—Robert A. Hafer
Assistant Examiner—Kathleen D'Arrigo
Attorney, Agent, or Firm—Gravely, Lieder & Woodruff

[57] ABSTRACT

A cushion device shaped into a configuration suitable for supporting the foot and ankle in a normal position or for supporting the elbow, and comprised of a flexible sheet material having adjacent major and minor panels joined by a web to allow the panels to be formed into the necessary shape to match the normal angular position of the foot and ankle, or elbow bend. The sheet material is provided on one surface with an array of pressure fluid cells organized to give the necessary support without causing the formation of sores usually associated with long periods of inactivity of movement. The sheet in its shaped configuration is secured by adjustable cooperating devices of the Velcro type.

11 Claims, 12 Drawing Figures

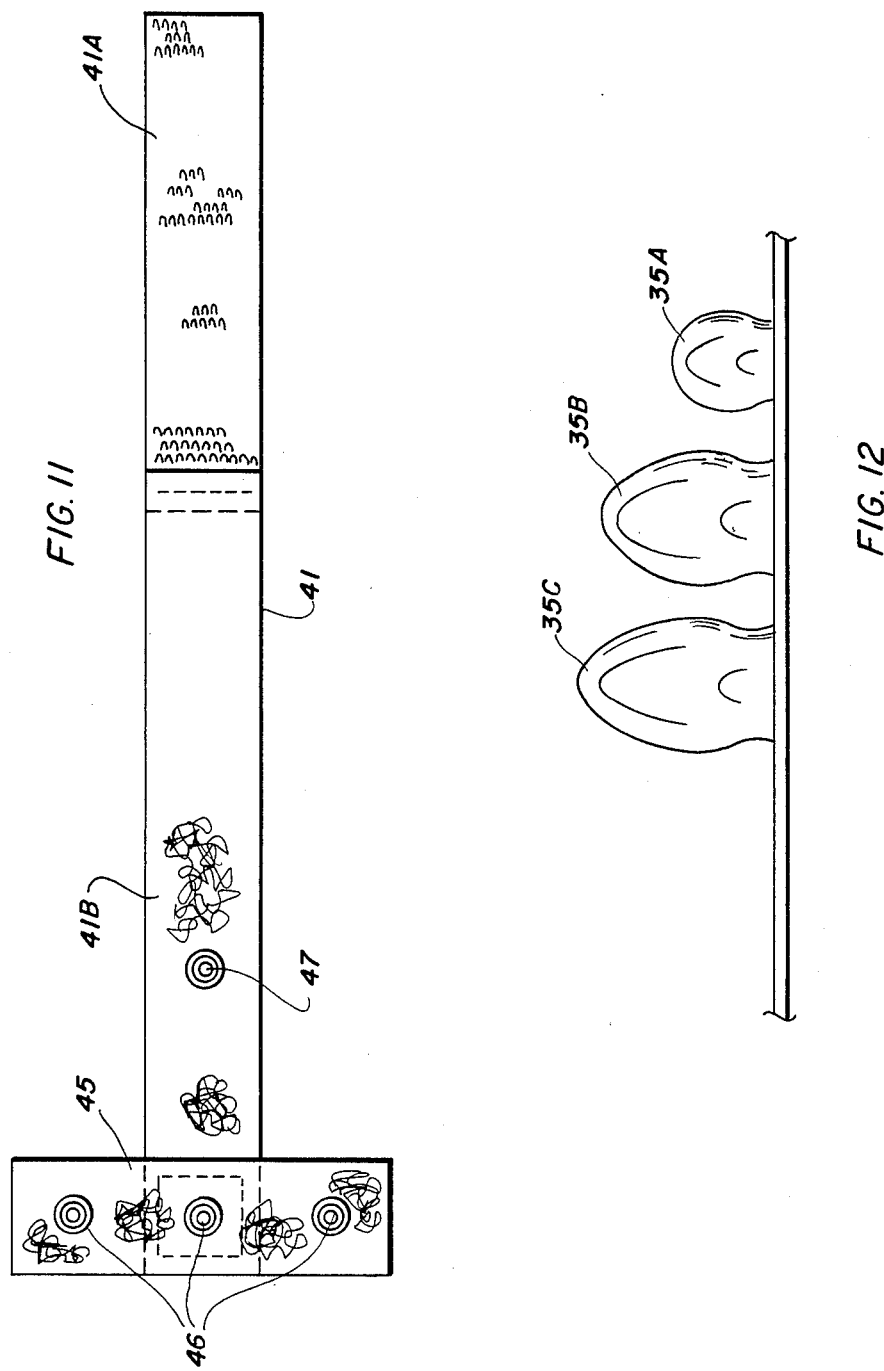

FOOT AND ELBOW CUSHION DEVICE

RELATED APPLICATION

This application is a continuation-in-part of application Ser. No. 730,467 of Robert H. Graebe filed May 6, 1985, and entitled FOOT AND ELBOW CUSHION DEVICE, now abandoned.

BACKGROUND OF THE INVENTION

1. Field of the Invention

This invention relates to cushion devices, and particularly to cushion devices for facilitating the healing of a wound through support of the heel of a foot or an elbow.

2. Description of the Prior Art

It is known to provide protective pads for parts of a human body subject to bedsores because of long periods of confinement to bed. Such pads are usually made with soft elastic material. Good examples are disclosed in U.S. Pat. Nos. 3,216,417 of Nov. 9, 1965; 3,721,237 of Mar. 20, 1973; 3,490,450 of Jan. 20, 1970; and 4,471,770 of Sept. 18, 1984.

It is seen that body support cushions having inflatable cells have been disclosed in U.S. Pat. Nos. 3,605,145 of Sept. 20, 1971 and 4,005,236 of Jan. 25, 1977.

The problems with the types of protective pads made up of flexible materials is that they present continuous surfaces which do not fully conform to the shape of the body, nor can any generate hydrostatic counter forces. They also rub on the body when body movement occurs. The friction effect is quite similar to plain bed sheets which are known to cause tissue damage leading to the development of bedsores. Thus, the use of soft flexible materials including lambs wool pads, as in the prior U.S. Pat. No. 4,471,770, has not solved the problem of eliminating bedsores since they do not generate a high degree of synthesis of fluid floatation, nor can they effectively facilitate the healing of a bedsore.

An improved approach to the problem of eliminating bedsores, as well as facilitate the healing of an open wound is disclosed in the body support cushion device that presents an array of fluid inflated cells forming a support surface. In such cushion devices each cell has six degrees of freedom and are distributed over an area of a size to accommodate the portion of the body and producing an adjustable hydrostatic like support through adjusting the pressure in the cells. The pads can be made flat which are then easily shaped to the contour of human feet or elbows. There is also a need for pads that have the ability to be preconformed to various shapes and therefore the pads can be formed into concave shapes having spherical dimensions.

BRIEF SUMMARY OF THE INVENTION

Important objects of the present invention are to provide a body support cushion device that can be shaped to suit different sizes of human feet or elbows, and to provide a support cushion device that can be applied in either of two positions as the need requires.

It is another object of the present invention to provide an array of fluid filled cells distributed over the surface of the device which constitutes the cushion, and to vary the heights in selected areas to adapt the cushion to the individual need, whether it is the heel of a foot or the shape of the bent elbow.

Other objects of the present invention are to construct a cushion device with parts that can be brought into a variety of shapes and to arrange an array of cushioning elements, such as inflatable cells which will allow easy shaping of the parts without sacrificing the desired support to be obtained by the cells.

The invention is preferably embodied in a cushioning device of general channel or sleeve configuration closed at one end, the device being initially a sheet of flexible and or elastic material in flat form having major and minor panels of rectangular shape connected by a web extending from one lengthwise margin of the major panel to a lengthwise margin of the minor panel and centered along the lengthwise margins to provide spaces between the panels. The sheet carries on one surface an array of cushion elements such as fluid filled cells, spaced apart and extending over part of said minor panel to leave open areas across the ends of said minor panel and to extend over substantially all of said major panel. There are cooperative attachment means on the end areas of the minor panel and on the opposite surface of the major panel opposite the surface presenting the array of cells, and other means on that opposite surface along the margins of said major panel adjacent the spaces between the panels, the attachment means being releasibly engageable to bring said minor panel end areas into engagment with the opposite surfaces of the major panel to hold the flat sheet in a sleeve shape terminated at one end by the minor panel and the fluid filled cells arranged on the inner surface of the sleeve shape. The widthwise margins of the major panel being further interconnected by detachable means to hold the major panel in its sleeve shaped configuration.

BRIEF DESCRIPTION OF THE DRAWINGS

A presently preferred embodiment of the cushioning boot is illustrated in drawings, wherein:

FIG. 11 is a view of the securing strap for the cushion device of FIG. 9 to illustrate it detachability; and FIG. 12 is a fragmentary sectional view taken along line 12—12 in FIG. 9 to illustrate the provision of sizing the cushioning cells.

DETAILED DESCRIPTION OF THE EMBODIMENT

Figure 1:
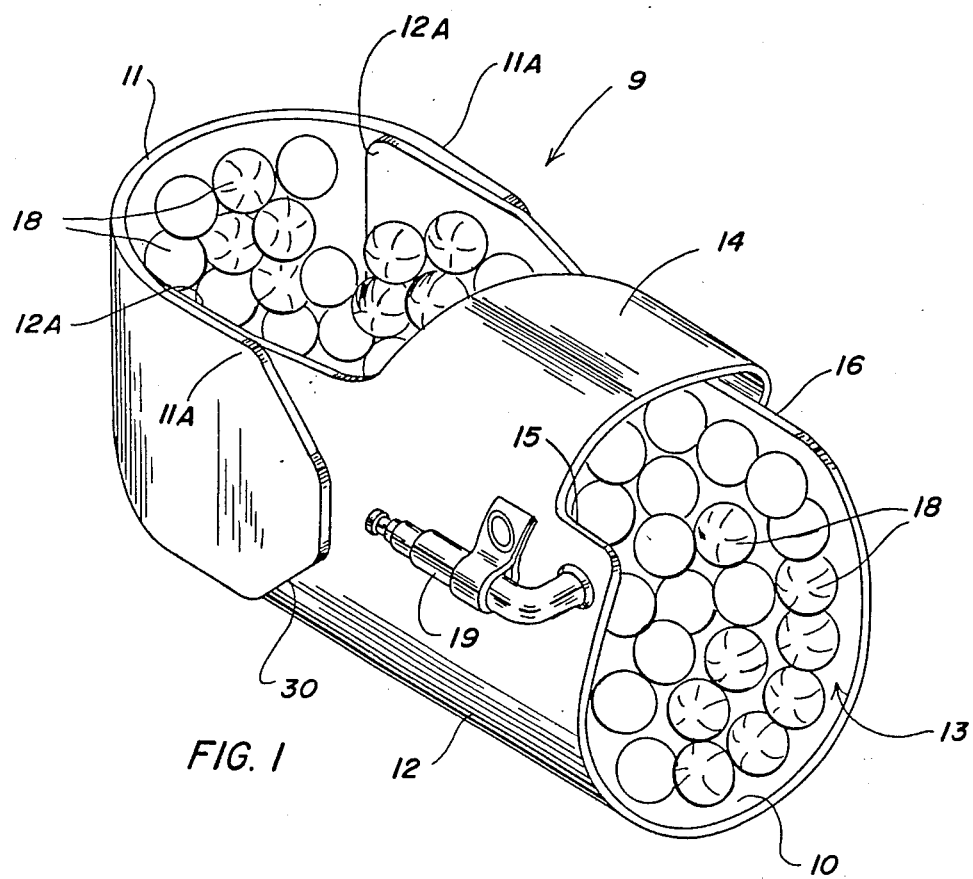
FIG. 1 is a perspective view of the cushion device in its sleeve shaped configuration.

The cushioning device 9 shown in FIG. 1 comprises a preformed sheet material 10 having a closure 11 and an elongated sleeve 12 in which the opposite margins 11A of the closure are attached to adjacent margins 12A of the sleeve in the manner shown in the drawing. The attachment is made up of cooperating Velcro pads of known character. In attaching the margins 11A of the closure 11 to the adjacent margins 12A of the sleeve 12, the configuration assumed thereby forms the sleeve 12 into a receiving channel 13 which allows the placement of a body part within the channel 13 and against the closure 11. For example, the foot and ankle of a long term bed patient may easily fit into the device 9 with the sole of the foot resting against the closure 11 and the ankle, achilles tendon and lower portion of the leg resting in the channel 13 of sleeve 12. The device 9 can then be secured in place by means of a flap 14 brought across the sleeve 12 from a margin 15 and extending from that margin of the sleeve 12 and secured by Velcro attachment means, as will appear presently, behing the opposite margin 16.

Figure 4:
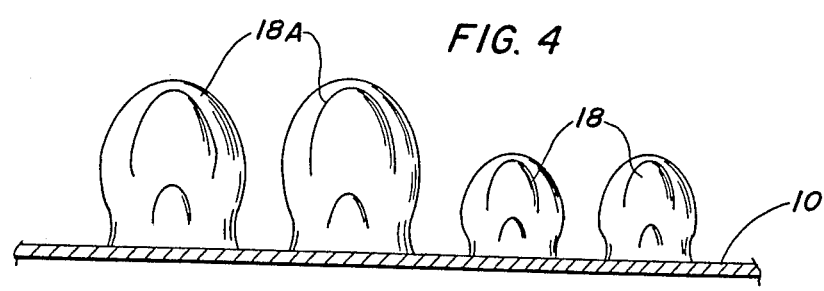
FIG. 4 is a fragmentary sectional view taken along line 4—4 of FIG. 2 showing the optional variation in the height of certain of the fluid filled cells.

The inner surface of the device 9 (FIG. 2) is characterized by the formation of a plurality of fluid filled cells 18 which are interconnected by small passages P in the plys of the sheet material 10. The small passages P may be formed by the presence of small strips laid in between the plies of the sheet material 10 in the panels 20 and 30, all as shown in my multicell cushion U.S. Pat. No. 4,541,136 issued Sept. 17, 1985 and incorporated herein by reference, or by molded passages P in the preformed sheet 10. These passages provide a uniform counter force effect and the resulting hydrostatic like support acting against the soft tissues of the foot and ankle, or an elbow. A filling valve assembly 19 is provided on the outer surface of the sleeve 12 for the purpose of admitting a fluid, such as air for filling the cells 18. Several filling valves can be provided to service an entire array or segregated groups of cells. The flexible sheet material having the flexible fluid filled cells formed to extend from an inside surface thereof is formed in the manner disclosed in the prior U.S. Pat. No. 3,605,145 of Sept. 20, 1971, and that disclosure is incorporated herein by reference. It is understood that in the forming of the cells the mold may be provided with certain longer projections forming the cells 18A, while the remainder of the projections form shorter inflatable cells 18. The difference in the length of the cells 18A compared to the cells 18 is illustrated in FIG. 4.

Figure 2:
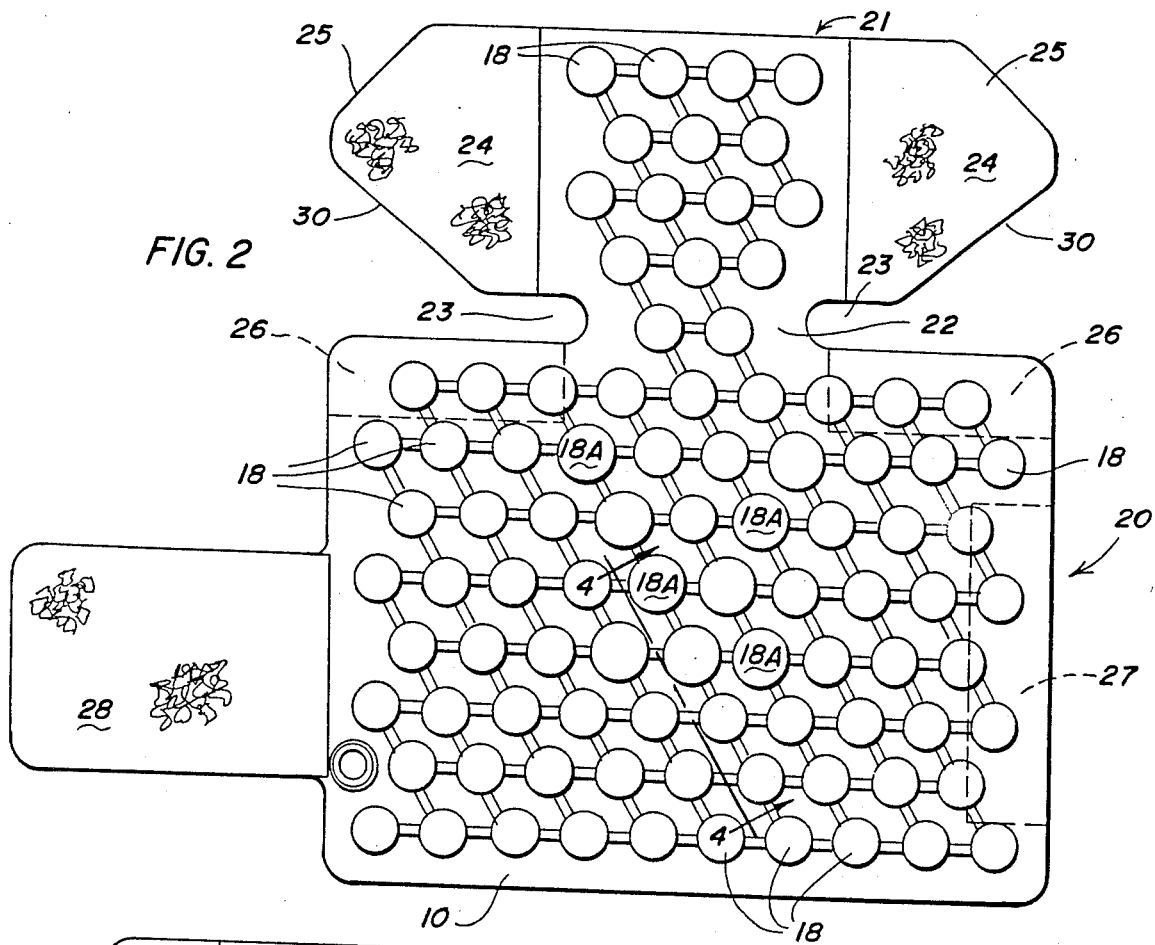
FIG. 2 is a view of the cushion device shown in the flat layout of the sheet material before it is brought into its sleeve configuration.

Turning now to FIG. 2, there is shown in a flat layout of the flexible sheet of material 10 composed of a major panel 20 of rectangular shape for the sleeve 12 shown in FIG. 1 in which the length of the panel is greater than the width. There is a minor panel 21 also of rectangular shape for the closure 11 having a length shorter than the length of the panel 20 making up sleeve 12, and in which that length is greater than its width. The major and minor panels 20 and 21 respectively are mechanically interconnected by a web 22 having a length considerably less than the lengthwise dimension of the minor panel 21 so as to provide a separation space 23 on each side of the web 22. Though not shown to simplify the drawing disclosure, it can be understood that in providing fluid filled cells having different working pressures, several valve assemblies, like the ones at 19 and 38, can be incorporated in the cushion device as at 38A, and when so used the groups of cells must be independent and connected to its own valve assembly. Accordingly, with this in mind, panel 32A can be pneumatically isolated from panel 32 so that two different working pressures can be realized. The face surface of the major and minor panels, seen in FIG. 2, is characterized by the presentation of the fluid filled cells 18 arranged so that opposite tabs or widthwise blank areas 24 of the minor panel 21 are free of the fluid filled cells. These blank areas provide for the reception of pads of Velcro hoops 25. The area of the major panel 20, and web 22, is almost entirely taken up with inflatable cells 18, except that there is an optional arrangement of a group of cells 18A that project upwardly or farther from the surface of major panel 20 to a somewhat greater extent than the other cells 18 (see FIG. 4). The higher fluid filled cells 18A are arranged in a V-shaped group near the center area of the major panel 20 for the purpose of forming a shaped area which provides a support within the device to conform to the contour of the heel to adjust the internal working pressure of the pad.

A particular advantage of the V-shaped arrangement is that there is a visual means created to determine that the correct internal pressure has been selected or obtained. The correct pressure is realized when the heel just touches or engages the other, or lower, cells by about fifty percent, or so. The medium height cells engage the achilles tendon region and form a "V" arrangement which encloses adjacent low height cells. It is in this "V" area that the heel should be placed. Extending from the "V" area are more low height cells to wrap up along the sole of the foot and side flap cells to wrap around the ankle when the heel pad is fully assembled.

Keeping a heel pad, or elbow pad, in proper position is a major problem with all other designs, but the present design allows the outer shell to have limited movement without relative cell motion on the skin. To enhance positional stability of the device, the outer or exposed surfaces of the device is made slick so it will slide easily over a bed sheet in response to movement of the foot or elbow. The effect of the slick surface is to avoid having the foot or elbow move within the device and fail to obtain the effectiveness of the support provided by the device.

The present device is constructed to provide an adjustable therapeutic counterpressure environment to the heel or elbow to facilitate the healing of an ischemic heel ulcer. A balance of distributed suspension forces is realized by the unique array of inflatable air cells which provide hydrostatic-like loads on the soft tissues to uniformly transfer suspension loads to the skeletal elements involved. Hydrostatic loading minimizes the deformation (friction and shear) of the soft tissues which aids in maintaining perfusion while supplying proper counterpressures to control edema. The cells should be in an overinflated state before placing a foot or elbow in the device, then adjustments can be made depending on the presence of bandaging, stocking bulk and the like.

It is apparent from the drawing (FIG. 1), that when the major panel is folded into its sleeve shape, the organization of fluid filled cells 18 and 18A will furnish a supporting surface that is capable of moving with the ankle and foot so as to avoid the rubbing reaction that has heretofore caused problems leading to bedsores or to the prevention of healing of bedsores. It is believed that the arrangement of the cells 18 and 18A will also provide a grip on the body part mounted in the cushion device 9 so as to move with the body part which is a further feature of importance that avoids the rubbing reaction of other devices. The reason is the cells track with skin movement. Furthermore, the V-shaped cell arrangement may be varied to assume a different shape, as a U or curved configuration.

Figure 3:
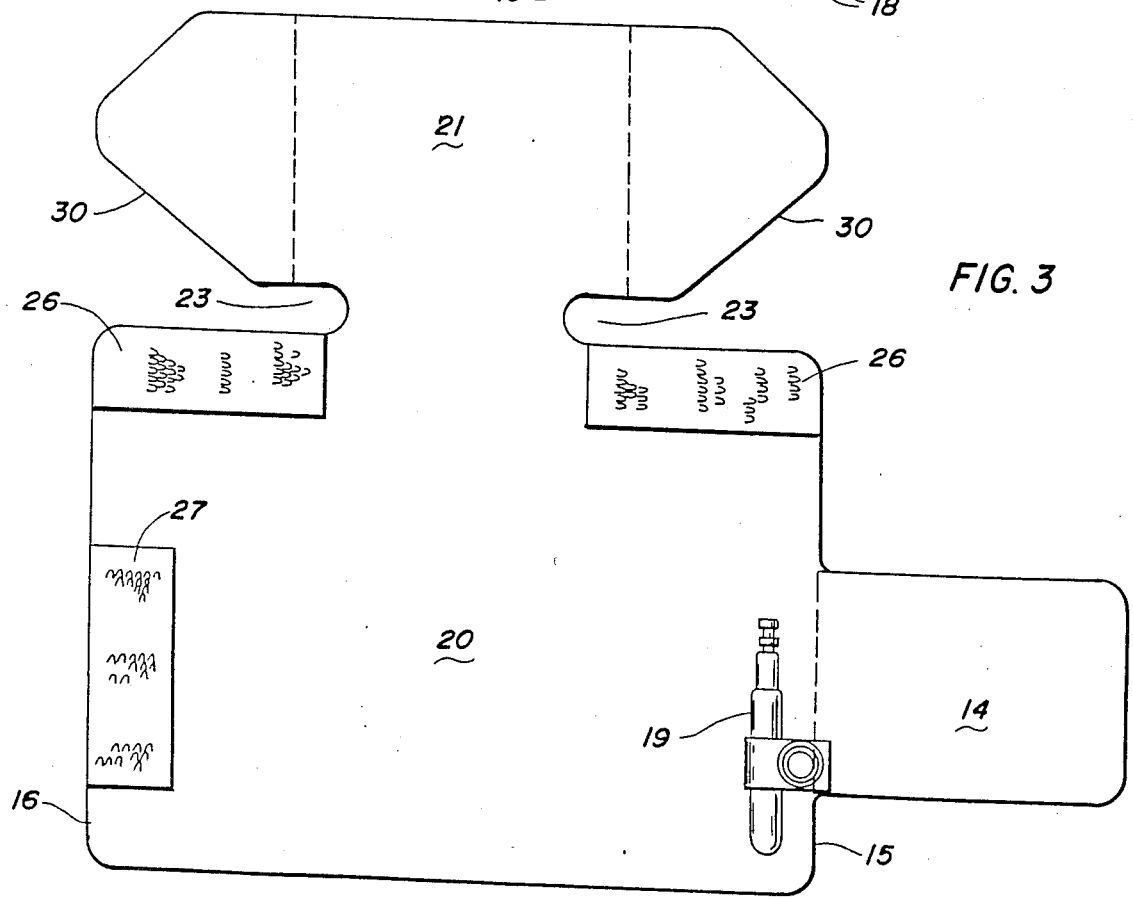
FIG. 3 is a view of the side opposite the one side seen in FIG. 2.

Turning now to FIG. 3, there is shown the opposite side of the major and minor panels 20 and 21 respectively so as to disclose a provision along the margins of the major panel 20 adjacent the spaces 23 where the Velcro hook pads 26 are located. The pads 26 are adapted to cooperatively attach themselves to the Velcro loop pads 25 mounted in the areas 24 on the minor panel 21 as indicated in FIG. 1. This opposite surface of the major panel 20 carries tha attachment tab 27 which cooperates in connecting itself to the Velcro loop pad 28 on the flap 14. The flap 14 has a suitable length to accommodate the wrap around effect of the sleeve 12 adjacent the receiving opening 13 with the flexible sheet material folded to form the cushion device 9 of FIG. 1. The cooperating parts of the Velcro attachment means are elongated so as to permit adjusting the size of the cushion device.

It has been pointed out above that the Cushion device 9 is suitable for supporting the foot and ankle of a patient confined for a considerable length of time to a bed. The device therefore is intended to facilitate healing of an open wound and to reduce the formation of bedsores. It is immediately apparent that the device 9 can be used in either of two positions. One position receives the ankle in the sleeve 12 and the sole of the foot adjacent the closure 11. The alternate position is reversed so that the sleeve 12 is in position to receive the foot and the ankle passes out at the closure 11. While the view of FIG. 1 illustrates a single flap 14 to secure the device in a sleeve configuration, an alternate is to employ a padded flap and suitable securing means.

Figure 5:
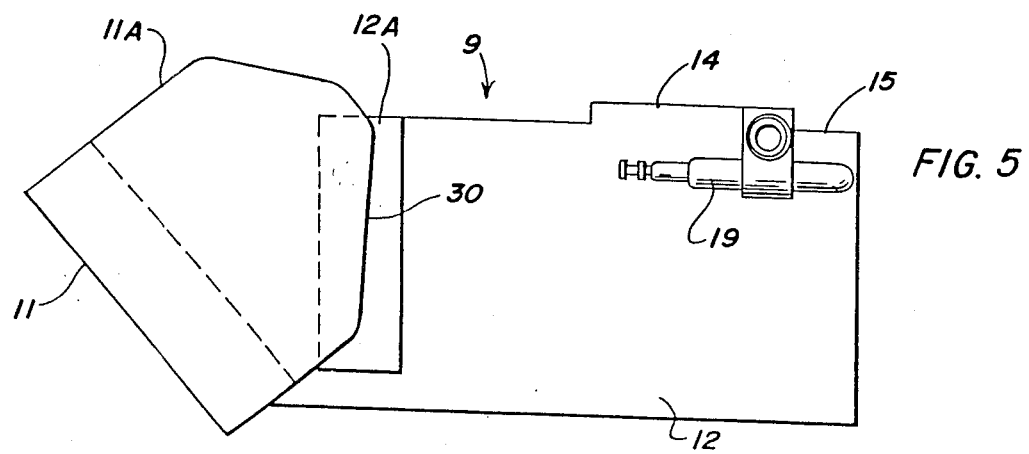
FIG. 5 is a side view of the cushion device adjusted to a position suitable of use in support of an elbow.

It is also contemplated that the cushion device 9 could be utilized to support the elbow so as to reduce the formation of bedsores. The view of FIG. 5 is an example of the adjustment of the cushion device 9 to accommodate the normal bend position of the arm at the elbow. It is seen that the angled margins 30 of the minor panel 21 allow for suitable positioning of closure 11 relation to the sleeve 12. Other uses of the cushion device 9 may come to mind as the principles of the foregoing disclosure are better understood.

Figure 6:
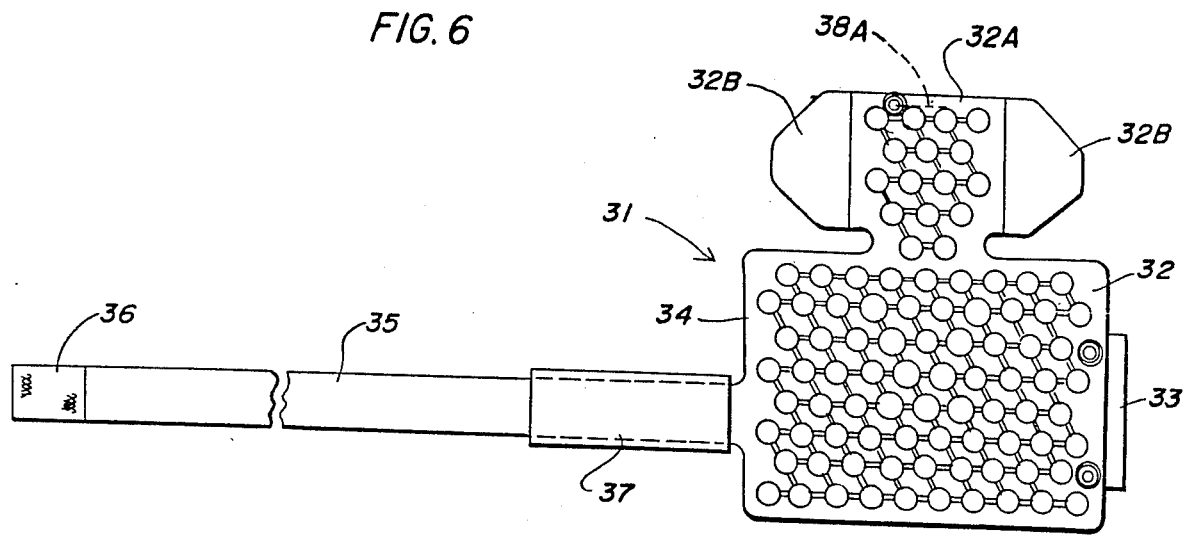
FIG. 6 is a flat layout of a modified cushion device.

FIG. 6 is a flat layout of the sheet material of a modified cushion device 31. While the general plan is similar to the view of FIG. 2, the modification resides in providing a strap 33 on the outside of the device 31 and securing its end portions by grommets so the central length is free of the device 31. The opposite margin 34 of the device 32 from the margin where the strap 33 is located is provided with an elongated strap 35 which is smooth on its upper surface (seen in FIG. 6) and is provided with an elongated Velcro patch on its underside. The end of the strap is provided with a Velcro hook patch 36 on the smooth side. The base of the strap 35 carries a pad 37 to protect the user's foot or leg from contact with the strap. The device 31 is made up of a first sheet of flexible material 32 and an extension 32A on which laterally directed tabs 32B are formed. The tabs carry Velcro loop patches and the sheet 32 carries Velcro hook patches. These patches are located as shown in the embodiment of FIG. 2 but are not included in FIG. 6 to simplify the disclosure.

Figure 8:
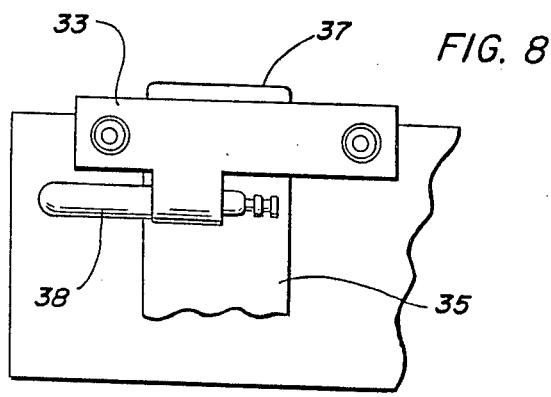
FIG. 8 is a fragmentary side view taken along line 8—8 in FIG. 7.
Figure 7:
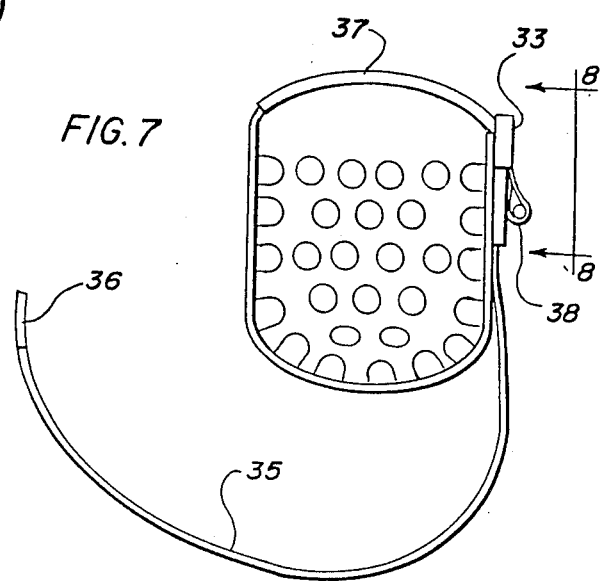
FIG. 7 is an end view of the cushion device when in its channel configuration.

As shown in FIGS. 7 and 8, the modified cushion device 31 is held in its channel configuration by feeding the strap 35 under the strap 33 so it passes beneath the inflation stem 38 and there encircles the device 31 to hold down the stem 38 before pressing the hook patch 36 against the loop patch of the strap 35 to complete the Velcro anchor. As seen in FIG. 8, the inflation stem 38 is retained in position by a loop 39 of the strap 33 encircling the stem to hold it in place lying along side the surface of the device 31. The strap 35 has sufficient length so it may be adjusted in its wrap about the device 31 to suit the needs for a snug or loose fit, as may be selected, to provide the cushioning effect.

In either embodiment of FIGS. 1 or 6, the flexible sheet material is seen to have an array of individual cushioning elements on one surface that becomes the inner surface when the sheet is folded into its channel configuration. It is also evident that there is a flexible sheet that, in effect, is an extension of the larger flexible sheet and it is foldable into a position closing one end of the channel configuration of the larger sheet. In FIG. 1, the device 9 is provided with a wide flap 14 as a securing means. However, the flap 14 leaves the inflation stem 19 exposed. In the device 31, the securing means is an elongated strap 35 which encircles the device and also covers most of the inflation stem 38 to hold it close to the surface of the sheet.

Figure 9:
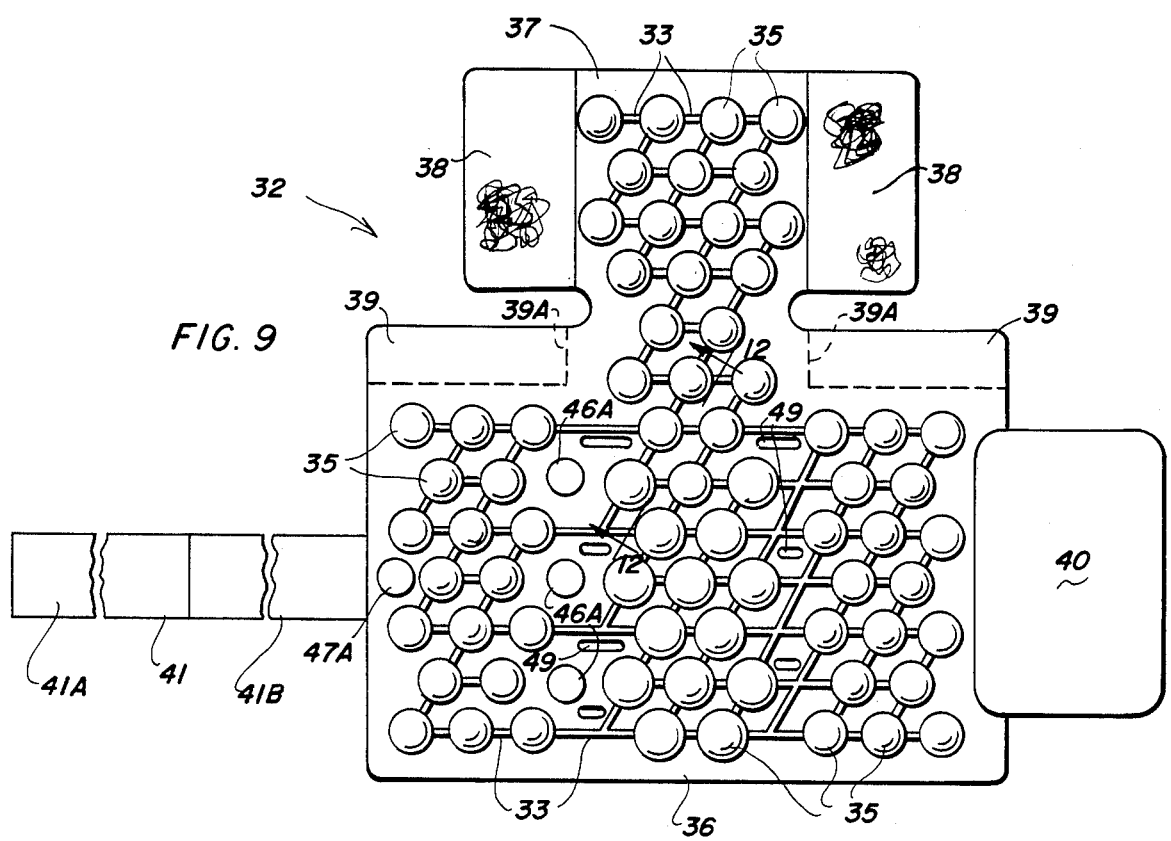
FIG. 9 is a plan view of a modified cushion device as seen from the cellular side thereof.
Figure 10:
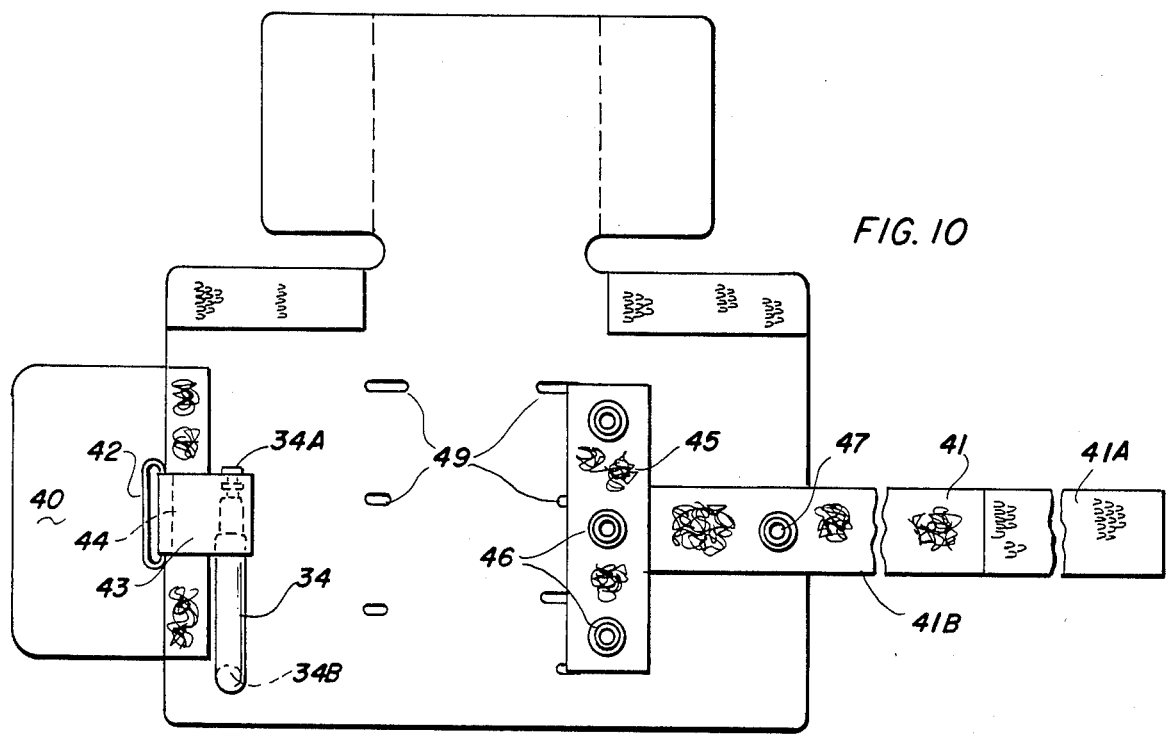
FIG. 10 is a plan view of the modified cushion device of FIG. 9 as seen from the opposite or outer side.

Turning now to FIGS. 9 and 10 there is shown a modified cushion device 42 fabricated of sheet material preformed with fluid passages 43 which afford communication from the filling valve assembly 44 to the inflatable cushion cells 45 distributed over the surface of the major panel 46 and minor panel 47 of the device 42. It is indicated in FIG. 9 that the respective inflatable cushion cells 45 are placed in fluid flow communication through an array of passages 43, and those passages are interconnected with a valve assembly 44 having its end 44a interconnected with the cell 45a by an extension that passes through the sheet material forming the major panel 46. This connection is similar to the one shown and described in connection with FIGS. 1 and 5.

It is noted in comparing FIGS. 2 and 9 that the cushion device of FIG. 9 is modified in comparison to FIG. 2 in that the minor panel 47 has rectangular flaps 48, and the surfaces seen in FIG. 9 carry patches of Velcro loop material which is intended to cooperate with the typical Velcro hook patches that are indicated at 49 on the underside of the panel 46. The Velcro components 48 and 49 are intended to cooperate with each other on the opposite sides of the cushion device when the major panel has been folded upwardly along lines that coincide in general with the inner ends 49A of the patches 49. When these portions of the major panel are folded upwardly it can be appreciated that the loop patch 48 can be brought into engagement with the hook patches 49 which are shown in FIG. 10, thereby creating a U-shaped structure in which the array of inflatable cells are inwardly directed to form a cushion for either the heel and ankle portion of a foot, or the bent elbow of a person's arm wherein the back of the elbow along the upper arm will be resting against the cells 45 of the minor panel 47 and the forearm will be resting on the cells 35 between the raised sides.

In comparing FIGS. 9 and 10, it is seen in FIG. 9 that there is a protective flap 50 along the right hand margin of the major panel 46, and a securing strap 51 projects leftwardly from the left margin of the major panel 46. The strap 51 is shown in foreshortened position as it has considerable length that will appear presently. In FIG. 10 the cushion device of FIG. 9 has been turned upside down so that the flap 50 is now at the left of the view of FIG. 10 and the strap 51 is now at the right. The reason for the protective flap is now apparent as it furnishes a surface to prevent a D-ring 52 from coming into contact with the arm or leg of a patient utilizing the cushion device. The D-ring is secured by a retainer loop 53 which wraps around the inlet end 44A of the valve assembly 44 and then is folded back on itself and is caught in a stitch seam 54. It is also seen in FIG. 10 that the securing strap 51 has the base of its inner end 51B; attached to a transverse holding element 55. The holding element is attached to the outer surface of the major panel 46 by three spaced apart snap fittings 56 each of which is adapted to engage in a respective receiver element 56A which are indicated in FIG. 9. There is an additional snap fastener 57 between the strap 51 and its cooperating counterpart 57A which is seen in FIG. 9. The reason for the snap is to permit the strap and its retainer 55 to be removable when the cushion device requires cleaning and/or sanitation treatment.

In the foregoing description relative to FIG. 9, it was pointed out that the side portions of the major panel 46 are intended to be folded up along lines corresponding to the inner ends 49A of the Velcro hook patches 49. When that positioning of the sides of the major panels occurs, the strap 51 will be in a position to pass across the outer surface of the protective flap 50 and be threaded through the D-ring 52 before being reversed and redirected across the cushion device where it will be secured in holding position by means of the Velcro components which are mounted on the strap 51. In the view of FIG. 10 the strap 51 is seen to be provided with the Velcro hook components in the area 51A, and inwardly the loop patch components are shown in 51B. This arrangement permits the strap 51 to be passed through the D-ring 52 so that the outer end portion carrying the hook element 51A can be folded back over the felt portion 51B to make contact for retaining the cushion device in its applied position.

The details of the securing strap 51 and its retainer 55 are illustrated in FIG. 11 to indicate that it is a removable part of the cushion assembly.

It has been indicated in FIG. 9 that the inflatable cells 45 are shown in sectional elevation in FIG. 12 wherein the cells are graduated in size so that the shortest cell 45A assumes a position substantially adjacent the junction where the minor panel 47 attaches to the major panel 46. That short cell 45A is surrounded by a group of five somewhat longer cells 45B arranged in a triangular pattern, and outwardly of the cells 45B there are a group of 14 cells 45C that are the tallest.

The modified form of the cushion device which is illustrated in FIGS. 9 and 10 embodies the unique function of being able to adjust the amount of pressure in the various cells 45-45C to accommodate the size and weight of a foot and ankle or of an elbow to establish a desired support that will avoid the problems connected with the use of pads illustrated in the prior art before identified. Since the inflatable cells have six degrees of movement they will collectively create a floating cushion for the foot or elbow that will permit a sufficient degree of movement of those portions of the human body without creating a rubbing injury to the skin. This is a particularly important feature as the cushion device is intended for long term application, and is particularly adapted to prevent the creation of bedsores when a person must be confined to a bed for a long stretch of time.

It is seen in FIGS. 9 and 10 that there is provided a series of air vents 59 which are spaced along the area of the major panel where the sides of that panel are folded. These vents permit air to circulate either across the elongated cells 45C or the shorter cells 45A at each side thereof. Movement of an elbow or foot in the cushion device will force the cells to move in one or several directions of six degrees of freedom, thereby creating a sort of pumping action for moving air through the vents 59.

While the disclosure is seen with the inflation stem 19 or 38 at a side of the channel configuration (FIG. 1), it is recognized that there may be other locations, as at 38A in FIG. 6, on the cushion devices 9 or 31 that would be more satisfactory, or desirable if different pressures are needed, as for example on the minor panel 21 or the extension. The valve assembly 44 of FIG. 10 does not easily lend itself to relocation. Different pressures in the major and minor panels are desirable when the cushion device of either FIG. 1 or FIG. 6 is used as a walking cushion. It is also recognized that the major and minor panels may be substantially the same size, but those terms have been used for convenience in claiming the panels. Moreover, it is preferred, as seen in FIG. 8, to so restrain the inflation stems, wherever used, so there is eliminated the chance of a stem hitting the opposite foot or catching on bed clothing. In the instance where the cushion device is to be used as a walking cushion, the outer ply of material may be more rigid to form a shell that will hold a suitable shape. It is to be recognized that dimensional characteristics can be varied so as to meet size requirements of persons needing the device to prevent bedsores.

What is claimed is:

1. A cushion device for supporting a part of a human body such as a foot or elbow, said cushion device comprising:
   (a) flexible sheet material having face and back surfaces and being shaped initially in flat form to provide a major panel, a minor panel smaller than said major panel, and a web joining said major and minor panels;
   (b) cushion means carried by said face surface of said major and minor panels, said cushion means consisting of an array of pressure fluid containing cells distributed over the face surfaces of said major and minor panels and being in spaced apart arrangement and projecting outwardly to different heights from said face surface to present a plurality of individual support surfaces to the human body part, said cells having freedom of movement to adapt the surfaces thereof to move with the motion of the body parts supported thereon;
   (c) first cooperating attachment means carried by and between said major and minor panels for securing said minor panel in position to form said major panel into a partial channel configuration; and
   (d) second cooperating attachment means carried by said major panel in position for further shaping said major panel into a channel configuration.

2. The cushion device of claim 1 wherein said first cooperating attachment means includes Velcro patches on the face surface of said minor panel at each side of said web, and cooperating Velcro patches on said major panel at each side of said web and on the back surface such that said Velcro patches on said minor panel engage said Velcro patches on said major panel and embrace said major panel from said opposite surface.

3. The cushion device of claim 1 wherein said second cooperating attachment means includes a flexible member extending outwardly from a margin of said major panel to reach the opposite margin, and means on the opposite margin to retain said flexible member so that the major panel is releasibly fixed in said channel configuration.

4. The cushion device of claim 1 wherein said first and second cooperating attachment means are selectively adjustable to conform the channel configuration of said panels to suit a human body part.

5. The cushion device of claim 1 wherein said array of pressure fluid containing cells include a group of such cells in said face surface of said major panel arranged in a V-configuration and having a height dimension differing from others of said cells.

6. The cushion device of claim 1 wherein said array of cells in said face surface project to different heights from said major panel, certain of said array of cells being arranged in a V-configuration define a support area and have a greter height then other adjacent cells for supporting a body part adjacent a bend of such body part.

7. A cushion device formable into a sleeve configuration for supporting a foot or elbow body part, said cushion device comprising:
 (a) a sheet of flexible material having an inner and an outer surface;
 (b) cushion means carried by said inner surface of said panels consisting of an array or pressure fluid containing cells distributed over said inner surface of said panels and being in spaced apart arrangement and grouped according to height to present a plurality of support surfaces, certain of said groups having a V-configuration for selective support of a body part;
 (c) first securing means distributed between the inner and outer surfaces of said flexible material and so located as to form said material into a partial sleeve configuration closed at one end; and
 (d) other securing means operatively disposed on the outer surface of said flexible material in position to cooperate to complete the sleeve configuration, said other securing means being spaced from said closed end of said sleeve configuration.

8. The cushion device of claim 7 wherein said first and other securing means are each selectively engageable for altering the size of said sleeve configuration.

9. A cushion device for receiving a body part to be supported comprising:
 (a) a sheet of flexible material having an array of individualized and intercommunicated inflatable cushioning elements on one surface, said sheet being foldable into a sleeve configuration shaped to the body part to be received such that each cushion element of such elements has freedom to move with a body part;
 (b) a flexible extension member connected at one end to said flexible sheet and positioned when said flexible sheet material is folded into the sleeve shape to effect an end closure for the sleeve shape;
 (c) other individual cushioning elements carried on said extension member to cooperate with said first mentioned array of individual cushioning elements, certain ones of said first array of individual cushioning elements present a surface raised above the remainder of said individual cushion elements;
 (d) cooperating retainer means on said flexible sheet material and on said extension member for holding the sheet extension member in its position as an end closure for the sleeve shaped flexible sheet; and
 (e) means on said flexible sheet in position to communicate with said inflatable cushioning elements and adjust the pressure in said inflatable elements to provide hydrostaticlike loads on the soft tissues of a person's body part for transferring suspension loads to the skeletal elements of the body to the extent required for support of the body part.

10. In a cushion device for supporting and at least partially enclosing a human body part, said cushion device comprising:
 (a) flexible sheet material having an inner and an outer surface; said sheet material being foldable into an elongated U-shaped configuration with said inner surface partially closed at one end and open at the opposite end, said U-shape having a bottom and opposite opposed sides;
 (b) means on said sheet material in position for adjustably retaining the U-shaped configuration and partially closed one end in such configuration;
 (c) a first array of individual fluid filled cells distributed over said inner surface so as to be positioned on the bottom of said U-shaped configuration, and second arrays of individual fluid filled cells distributed over each of said opposite sides of said U-shaped configuration, said first array of fluid filled cells having certain of said cells therein arranged in adjacent positions so as to be formed into a V-shaped pattern in which the cells in said V-shaped pattern project from said inner surface farther than the cells of said first and second arrays; and
 (d) fluid pressure admission means on said sheet material in communication with said cells, whereby said first array of cells contain fluid pressure for supporting a body part in position such that the body part is variably supported by said V-shaped array of cells, and said second arrays support the sides of a body part.

11. The cushion device set forth in claim 10 wherein said outer surface of said sheet material has a lower coefficient of friction than said inner surface to permit substantial mobility of said cushion device simultaneously with movement of the body part.

* * * * *